United States Patent
Moriya et al.

(10) Patent No.: US 8,802,433 B2
(45) Date of Patent: Aug. 12, 2014

(54) MACROPHAGE PHAGOCYTOSIS-ACTIVATING COMPOSITION AND/OR COMPOSITION PROMOTING CYTOKINE PRODUCTION IN MACROPHAGES

(75) Inventors: Naoyuki Moriya, Kimitsu (JP); Yukiko Moriya, Kimitsu (JP); Yasuhiro Nikawa, Kimitsu (JP); Yukitoshi Nagahara, Hatoyama-machi (JP); Hidekazu Tamegai, Hatoyama-machi (JP); Tadaaki Miyazaki, Sapporo (JP)

(73) Assignee: Aureo Co., Ltd., Tokyo (JP)

( * ) Notice: Subject to any disclaimer, the term of this patent is extended or adjusted under 35 U.S.C. 154(b) by 0 days.

(21) Appl. No.: 13/512,502

(22) PCT Filed: Dec. 3, 2010

(86) PCT No.: PCT/JP2010/071747
§ 371 (c)(1),
(2), (4) Date: Sep. 11, 2012

(87) PCT Pub. No.: WO2011/068226
PCT Pub. Date: Jun. 9, 2011

(65) Prior Publication Data
US 2012/0329154 A1    Dec. 27, 2012

(30) Foreign Application Priority Data
Dec. 3, 2009   (JP) ................. 2009-275553

(51) Int. Cl.
| | | |
|---|---|---|
| C12N 5/07 | (2010.01) | |
| A61K 31/4745 | (2006.01) | |
| A61K 31/513 | (2006.01) | |
| C12R 1/645 | (2006.01) | |
| C12N 1/38 | (2006.01) | |
| A61K 36/06 | (2006.01) | |

(52) U.S. Cl.
CPC ........... *A61K 31/4745* (2013.01); *A61K 31/513* (2013.01); *C12R 1/645* (2013.01); *C12N 1/38* (2013.01); *A61K 36/06* (2013.01)
USPC ............ 435/375; 424/1.41; 424/102; 424/41; 424/343

(58) Field of Classification Search
CPC ................. C12N 2310/321; C12N 2310/3521; C12N 2310/14; C12N 15/1138; C12N 15/111; C12N 2310/3525; C12N 15/113; C12N 15/1131; C12N 1/38; C12N 2310/322; C12N 2310/3231; C12N 2310/331; C12N 2320/30; C12N 2320/51; C12N 2760/16111
USPC .............. 435/375; 424/1.41, 41, 373
See application file for complete search history.

(56) References Cited

U.S. PATENT DOCUMENTS

| | | | |
|---|---|---|---|
| 2002/0082418 A1 | 6/2002 | Ikewaki et al. | |
| 2004/0076633 A1* | 4/2004 | Thomsen et al. | .......... 424/184.1 |
| 2005/0235372 A1 | 10/2005 | Akira et al. | |
| 2005/0257280 A1 | 11/2005 | Akira | |
| 2005/0271613 A1 | 12/2005 | Suzuki et al. | |
| 2006/0105048 A1 | 5/2006 | Terada et al. | |
| 2009/0060870 A1 | 3/2009 | van der Burg et al. | |
| 2009/0060889 A1 | 3/2009 | von Hofe et al. | |
| 2009/0123493 A1 | 5/2009 | Ataman-Onal | |
| 2010/0068184 A1 | 3/2010 | Moriya et al. | |
| 2010/0178354 A1 | 7/2010 | Terada | |

FOREIGN PATENT DOCUMENTS

| | | |
|---|---|---|
| JP | 2000-247884 | 9/2000 |
| JP | 2002-204687 A | 7/2002 |
| JP | 2004-073073 A | 11/2004 |
| JP | 2006-104439 A | 4/2006 |
| JP | 2007-063287 A | 3/2007 |
| JP | 3947999 | 7/2007 |
| JP | 2008-539228 A | 11/2008 |
| JP | 2009-515859 A | 4/2009 |
| WO | WO03/043588 A1 | 5/2003 |
| WO | WO2007/069468 A1 | 6/2007 |
| WO | WO2008/053728 A1 | 5/2008 |
| WO | WO2008/112218 A2 | 9/2008 |

OTHER PUBLICATIONS

Colombo, Mario et al. Interleukin-12 in anti-tumor immunity and immunotherapy. Cytokine & Growth Factor Reviews 13. 2002. pp. 155-168.*
Daiso Co. JP 2006-104439A. 2006. Machine Translated from the JPO website on May 15, 2013.*
Tomai, Mark et al. The Immune Response Modifiers Imiquimod and R-848 Are Potent Activators of B Lymphocytes. Cellular Immunology 203. 2000. pp. 55-65.*

(Continued)

*Primary Examiner* — Susan Hanley
*Assistant Examiner* — Nghi Nguyen
(74) *Attorney, Agent, or Firm* — RatnerPrestia

(57) ABSTRACT

Disclosed is a highly effective macrophage phagocytosis-activating composition and/or composition promoting cytokine production in macrophages using an active component derived from natural products. A culture obtained by culturing microorganisms belonging to the genus *Aureobasidium* (*Aureobasidium* sp.) is used as the active component of the macrophage phagocytosis-activating composition and/or composition promoting cytokine production in macrophages. By means of the macrophage phagocytosis-activating composition and/or composition promoting cytokine production in macrophages, macrophage phagocytosis can be activated, and cytokine production in macrophages can be promoted. In particular, a macrophage phagocytosis-activating composition can activate the phagocytosis of cancer cells or cells damaged or destroyed by anticancer drugs.

1 Claim, 7 Drawing Sheets

(56) References Cited

OTHER PUBLICATIONS

ChemSpider: The Free Chemical Database. 4-amino-2-ethoxymethyl-α,α-dimethyl-H-imidazol[4,5-c]quinolone-1-ethanol). Downloaded from the ChemSpider webpage on May 15, 2013: <http://www.chemspider.com/Chemical-Structure.140330.html>.*

Bunshi Saibo Seibutsugaku Jiten, 1.ISR7, $1^{st}$ Edition, $1^{st}$ print, Mar. 10, 1997, p. 775.

Hemmi et al., Small anti-viral compounds activate immune cells via the TLR7 MyD88-dependent signaling pathway, Nat Immunol, 2002, vol. 3, No. 2, pp. 196-200.

International Search Report, dated Dec. 28, 2010, corresponding to PCT/JP2010/071747, filed Dec. 3, 2010.

* cited by examiner

SEQUENCE LISTING

<160> NUMBER OF SEQ ID NOS: 10

<210> SEQ ID NO 1
<211> LENGTH: 18
<212> TYPE: DNA
<213> ORGANISM: Artificial
<220> FEATURE:
<223> OTHER INFORMATION: sense primer

<400> SEQUENCE: 1
tccttcagac cctcaacc                                                18

<210> SEQ ID NO 2
<211> LENGTH: 20
<212> TYPE: DNA
<213> ORGANISM: Artificial
<220> FEATURE:
<223> OTHER INFORMATION: antisense primer

<400> SEQUENCE: 2
aggccccagt ttgaattctt                                              20

<210> SEQ ID NO 3
<211> LENGTH: 26
<212> TYPE: DNA
<213> ORGANISM: Artificial
<220> FEATURE:
<223> OTHER INFORMATION: sense primer

<400> SEQUENCE: 3
ttttctgcca gtgccagtgc ctcttt                                       26

<210> SEQ ID NO 4
<211> LENGTH: 20
<212> TYPE: DNA
<213> ORGANISM: Artificial
<220> FEATURE:
<223> OTHER INFORMATION: antisense primer

<400> SEQUENCE: 4 taccccagg agaagattcc                                               20

<210> SEQ ID NO 5
<211> LENGTH: 20
<212> TYPE: DNA
<213> ORGANISM: Artificial
<220> FEATURE:
<223> OTHER INFORMATION: sense primer

<400> SEQUENCE: 5
catgggcctt catggtattt                                              20

```
<210> SEQ ID NO 6
<211> LENGTH: 20
<212> TYPE: DNA
<213> ORGANISM: Artificial
<220> FEATURE:
<223> OTHER INFORMATION: antisense primer

<400> SEQUENCE: 6
tgatgtactt gcagccttgc                                               20

<210> SEQ ID NO 7
<211> LENGTH: 20
<212> TYPE: DNA
<213> ORGANISM: Artificial
<220> FEATURE:
<223> OTHER INFORMATION: sense primer

<400> SEQUENCE: 7
cagaccttcc agatcgcttc                                               20

<210> SEQ ID NO 8
<211> LENGTH: 20
<212> TYPE: DNA
<213> ORGANISM: Artificial
<220> FEATURE:
<223> OTHER INFORMATION: antisense primer

<400> SEQUENCE: 8
tcggattcca ggttttcatc                                               20

<210> SEQ ID NO 9
<211> LENGTH: 20
<212> TYPE: DNA
<213> ORGANISM: Artificial
<220> FEATURE:
<223> OTHER INFORMATION: sense primer

<400> SEQUENCE: 9
atcatcagca atgcctcctg                                               20

<210> SEQ ID NO 10
<211> LENGTH: 20
<212> TYPE: DNA
<213> ORGANISM: Artificial
<220> FEATURE:
<223> OTHER INFORMATION: antisense primer

<400> SEQUENCE: 10
ctgcttcacc accttcttga                                               20
```

MACROPHAGE PHAGOCYTOSIS-ACTIVATING COMPOSITION AND/OR COMPOSITION PROMOTING CYTOKINE PRODUCTION IN MACROPHAGES

CROSS-REFERENCE TO RELATED APPLICATIONS

This application is a U.S. National Phase Patent Application of PCT Application No. PCT/JP2010/071747, filed Dec. 3, 2010, which claims priority to Japanese Patent Application No. 2009-275553, filed Dec. 3, 2009, both of which are incorporated by reference herein in their entirety.

TECHNICAL FIELD

The present invention relates to a macrophage phagocytosis-activating composition and/or a composition promoting cytokine production in macrophages.

BACKGROUND ART

It is known that macrophage cells have phagocytosis, and this macrophage phagocytosis allows innate immunity such as ingestion, degradation and elimination of foreign substances such as pathogenic bacteria, and allows acquired immunity through the process of presentation of antigen information on the surface of macrophage cells, its transmission to T-lymphocytes, induction of specific antibody production and so forth. In addition, it is known that macrophages produce various cytokines, and the produced cytokines exhibit various actions such as regulating inflammatory responses and immune responses, inducing apoptosis, or acting as a hematopoietic factor or growth factor. Therefore, activation of the phagocytosis of macrophages or cytokine production in macrophages leads to enhancement of animal immunity, and substances effective for the activation are useful as an active ingredient of a new immunostimulator, immunomodulator, anticancer agent, anti-allergic agent, adjuvant for antibody production, or the like. They are particularly useful as an immunostimulator, immunomodulator, anticancer agent, or anti-allergic agent in which innate immunity or cellular immunity is involved.

Regarding substances effective for the activation of macrophage phagocytosis, the enhancement of phagocytic activity of macrophages by PLGA (poly(lactic acid/glycolic acid) copolymer), including PLGA with a molecular weight of 1,500 to 150,000, is described, for example, in the following Patent Literature 1 or 2. In addition, regarding substances for promoting cytokine production, the promotion of cytokine production by alginate oligomer prepared from sodium alginate is described, for example, in the following Patent Literature 3.

CITATION LIST

Patent Literature

Patent Literature 1: Japanese Patent Laid-Open No. 2007-63287
Patent Literature 2: Japanese Patent No. 3947999
Patent Literature 3: International Publication No. WO 2007/069468

SUMMARY OF INVENTION

Technical Problem

However, conventionally, a naturally occurring active ingredient has been hardly used in a composition for activating macrophage phagocytosis or a composition for promoting cytokine production in macrophages.

The object of the present invention is to provide a composition for activating macrophage phagocytosis or a composition for promoting cytokine production in macrophages using a naturally occurring active ingredient, which has excellent effects.

Solution to Problem

The present inventors have exhaustively studied to achieve the above object, leading to completion of the present invention. More specifically, the present invention is as follows.

[1] A composition for activating macrophage phagocytosis and/or a composition for promoting cytokine production in macrophages, wherein the composition comprises a culture obtained by culturing a microorganism belonging to *Aureobasidium* sp. as an active ingredient.

[2] The composition for activating macrophage phagocytosis and/or the composition for promoting cytokine production in macrophages according to the above [1], further comprising the following compound (1) or compound (2) as an active ingredient.

[Formula 1]

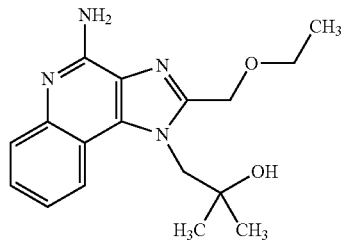

(1)

[Formula 2]

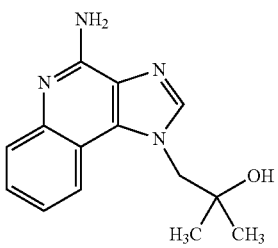

(2)

[3] The composition for activating macrophage phagocytosis and/or the composition for promoting cytokine production in macrophages according to the above [1] or [2], wherein the microorganism belonging to *Aureobasidium* sp. is *Aureobasidium pullulans* M-1 (FERM BP-08615) or *Aureobasidium pullulans* M-2 (FERM BP-10014).

[4] The composition for activating macrophage phagocytosis and/or the composition for promoting cytokine production in macrophages according to any one of the above [1] to [3], wherein the composition is applied to phagocytose the following cells (1) or (2):

(1) cancer cells, or
(2) cells damaged or killed by an anticancer agent, if it is a composition for activating macrophage phagocytosis.

[5] The composition for activating macrophage phagocytosis and/or the composition for promoting cytokine production in macrophages according to the above [4], wherein the anticancer agent is 5-fluorouracil (5-FU).

Advantageous Effects of Invention

According to the composition for activating macrophage phagocytosis and/or the composition for promoting cytokine production in macrophages according to the present invention, a culture obtained by culturing the microorganism belonging to *Aureobasidium* sp. and used as an active ingredient can activate macrophage phagocytosis, and can promote cytokine production in macrophages. Particularly, in the case of the composition for activating macrophage phagocytosis, its ability to phagocytose cancer cells, or cells damaged or killed by an anticancer agent can be activated.

DESCRIPTION OF EMBODIMENTS

Figure 1:
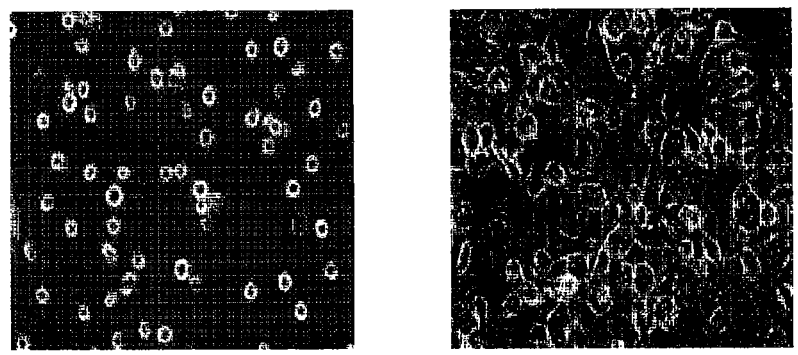
FIG. 1 is micrographs of THP-1 cells (A) and macrophage-like cells differentiated from THP-1 cells (B).

As a culture obtained by culturing the microorganism belonging to *Aureobasidium* sp. used in the present invention (hereinafter, referred to as "*Aureobasidium* culture"), a culture fluid itself produced by culturing the microorganism belonging to *Aureobasidium* sp. (hereinafter, referred to as "*Aureobasidium* microorganism"), a concentrate of the culture fluid, a dilution of the culture fluid, or a solid obtained by removing water from the culture fluid, and the like can be used, but the culture fluid itself or the concentrate or dilution of the culture fluid is preferably used.

The *Aureobasidium* culture used in the present invention can contain β-glucan produced by culturing the *Aureobasidium* microorganism as it is. The content of β-glucan in that case is preferably 50 to 2000 mg, more preferably 100 to 2000 mg, and most preferably 100 to 800 mg, in terms of the content based on 100 g by mass of the culture fluid itself.

Here, the β-glucan content described above can be determined, for example, by the following method. Specifically, a culture fluid is subjected to an enzyme treatment using amylase, amyloglucosidase, protease, and the like, to remove proteins and α-glucans such as pullulan, and then subjected to ethanol precipitation. Then, the precipitate is filtered with a glass filter to obtain a polymer sample. The sample is sufficiently washed with 80% ethanol in order to remove low molecular substances including monosaccharide. The washed polymer sample is further washed with acetone, and sulfuric acid is added thereto to carry out hydrolysis. After hydrolysis, the resulting sample is neutralized, and the filtrate is collected. The amount of glucose therein is determined by a glucose oxidase method, and the value calculated based on the following Expression 1 is defined as the amount of β-glucan.

β-Glucan (g/100 g)=Glucose (g/100 g)×0.9     Expression 1:

In addition, the β-glucan content can be also determined as the amount of what is called sugar chain-containing polymer substances (polysaccharides). In that case, a culture fluid is subjected to an enzyme treatment using amylase, amyloglucosidase, protease, and the like, to remove proteins and α-glucans such as pullulan, and then subjected to ethanol precipitation. Then, the precipitate is filtered with a glass filter to obtain a polymer sample. The sample is sufficiently washed with 80% ethanol in order to remove low molecular substances including monosaccharide. The washed polymer sample is further washed with acetone, and the weight of the resulting sample is measured as the amount of sugar chain-containing polymer substances (polysaccharides).

It is noted that β-glucan quantified as described above is quantified as the substance having functional groups such as a sulfate group and/or phosphate group. Therefore, when β-glucan is quantified as broad-sense sugar chain-containing polymer substances (polysaccharides) as described above, the content of β-glucan in the *Aureobasidium* culture produced by culturing the *Aureobasidium* microorganism is preferably 70 to 3000 mg, more preferably 140 to 3000 mg, and most preferably 140 to 1100 mg, in terms of the content based on 100 g by mass of the culture fluid itself.

The *Aureobasidium* microorganism used in the present invention may be any of microorganisms belonging to *Aureobasidium* sp., and for example, *Aureobasidium pullulans* M-1 (International Patent Organism Depositary, National Institute of Advanced Industrial Science and Technology (AIST Tsukuba Central 6, 1-1, Higashi 1-Chome Tsukuba-shi, Ibaraki-ken 305-8566 Japan), Accession No. of FERM BP-08615, date of deposit: Feb. 14, 2003) and *Aureobasidium pullulans* M-2 (International Patent Organism Depositary, National Institute of Advanced Industrial Science and Technology (AIST Tsukuba Central 6, 1-1, Higashi 1-Chome Tsukuba-shi, Ibaraki-ken 305-8566 Japan), Accession No. of FERM BP-10014, date of deposit: Apr. 22, 2004) are preferably used. It is noted that it has been revealed that β-glucan produced by these strains is β-1,3-1,6-glucan having a structure in which glucose is branched with β-1,6 linkages from a main chain with glucose joined by β-1,3 linkages according to the structural analysis by NMR measurement (13CNMR: Varian UNITY INOVA 500, 1HNMR: Varian UNITY INOVA 600).

Culture of the *Aureobasidium* microorganism can be carried out according to a known method (refer to Japanese Patent Laid-Open No. 57-149301). Specifically, bacteria may be inoculated on a medium (pH 5.2 to 6.0) containing 0.5% to 5.0% by mass of carbon source (sucrose), 0.1% to 5.0% by mass of N source, and other trace substances (for example, vitamins, inorganic substances), and cultured with aeration at a temperature of 20 to 30° C. for 2 to 14 days, and preferably cultured with aeration and stirring. When the β-glucan produced by culturing the *Aureobasidium* microorganism is directly contained, the viscosity of culture fluid increases with the production of β-glucan, and the *Aureobasidium* microorganism becomes gelatinous with high viscosity. The culture fluid obtained as described above normally contains 0.6 to 10% by mass of solid content, and β-glucan is contained in the solid content by 5 to 80% by mass. Since, in addition to β-glucan, for example, other useful components such as phosphorus, potassium, magnesium, and vitamin C, that are the components helping the action of glucan are also contained, β-glucan as well as the components of the *Aureobasidium* culture such as phosphorus, potassium, magnesium, and vitamin C harmonize to exhibit effects as the composition for activating macrophage phagocytosis according to the present invention or the composition for promoting cytokine production in macrophages according to the present invention, and also can efficiently exhibit physiological effects of β-glucan by useful components such as phosphorus, potassium, magnesium, and vitamin C.

In the present invention, the culture fluid obtained by the culture may be directly heated or subjected to pressurized heat sterilization and used, and may be sterilized and used after separating and removing a strain by centrifugation or the like. The culture fluid may also be concentrated or even dried as necessary prior to use. Furthermore, a component such as β-glucan can be also selectively extracted and used. The culture of a microorganism belonging to the *Aureobasidium* sp. is used as a food additive such as a thickening stabilizer, and is highly safe.

In the present invention, cytokines mean a type of proteins produced by cells, forming a group of humoral factors responsible for intercellular communication which act on a specific cell-surface receptor by a minute amount, and work for proliferation, differentiation and regulation of functional expression of the cells. Examples of the cytokines can include interleukin (IL), interferon (IFN), a tumor necrosis factor (TNF), a colony-stimulating factor (CSF), a transforming growth factor and chemokine. Specifically, examples of the colony-stimulating factor (CSF) can include G-CSF, GM (glanulocyte-macrophage)-CSF and M (macrophage)-CSF; examples of chemokine can include CXC chemokines [KC (keratinocyte derived chemokine: CXCL8), and the like], CC chemokines [MCP (monocyte chemoattractant protein)-1 (CCL2), MIP-1α (CCL3), MIP-1β (CCL4), RANTES (CCL5), Eotaxin (CCL11), and the like], C chemokines and CX3C chemokines; examples of interleukin (IL) can include IL-1α, IL-1β, IL-2, IL-3, IL-4, IL-5, IL-6, IL-7, IL-8, IL-9, IL-10, IL-11, IL-12 (p70), IL-12A (p35), IL-12B (p40), IL-13, IL-14, IL-15, IL-16, IL-17 and IL-18; examples of interferon (IFN) can includes IFN-α, IFN-β and IFN-γ; and examples of the tumor necrosis factor (TNF) can include TNF-α and TNF-β. The composition for promoting cytokine production in macrophages according to the present invention is not particularly limited, and the production of inflammatory cytokines such as TNF-α, IL-1, IL-6, IFN-γ, IL-8, IL-12, IL-12A, IL-12B, and IL-18 is particularly promoted.

A method known to one skilled in the art can be used for the formulation of the composition for activating macrophage phagocytosis and/or the composition for promoting cytokine production in macrophages according to the present invention. The dosage form may be a dosage form that can be properly selected also by one skilled in the art, and examples of such a dosage form can include forms such as a tablet, a granule, a powder, a capsule, a coating tablet, a liquid, and a suspension which are prepared as an oral dose preparation, and can include forms such as a gel agent, an inhalant, an injection, a drop, a suppository, spray, a patch, an ointment, and a cream which are prepared for parenteral dosage. The dose level can be properly set depending on the formulation, dosing route, and intended use of the pharmaceutical composition as well as the age, body weight, and symptoms of a subject to receive the composition.

As the applicable method, for example, those prepared as an orally administered agent can be, for example, orally taken, to exhibit the physiologically active effect from the body. Those prepared as a skin external preparation can be, for example, applied to the affected area, to exhibit the physiologically active effect.

The level to be dosed can be properly determined depending on a difference in purpose of treatment and prevention, dosage form, level of symptoms, patient age, dosing route, frequency of administration, timing of administration, and the like. The general effective dose level is, for example, when orally taken, it is taken in an amount of about 0.06 to 60 mg/kg (body weight) per day in terms of the amount of β-glucan.

When used as a food additive, the form can be properly selected, and examples can include those obtained by directly preparing as a food the composition for activating macrophage phagocytosis and/or the composition for promoting cytokine production in macrophages according to the present invention, those added to other foods, or any forms normally used for a food or health food, such as a capsule and a tablet. When it is added to a food prior to ingestion or administration, it can be properly mixed with an excipient, an extender, a binder, a thickener, an emulsifier, a colorant, a flavor, a food additive, a seasoning, and the like, and formed into a powder, a granule, a tablet, or the like depending on the intended use. Furthermore, it can be ingested by mixing it into the raw material of food to prepare a food which is then commercialized as a functional food.

The composition for activating macrophage phagocytosis and/or the composition for promoting cytokine production in macrophages according to the present invention may further contain the following compound (1) (4-Amino-2-(ethoxymethyl)-a,a-dimethyl-1H-imidazo[4,5-c]quinoline-1-ethanol) or the following compound (2) (imiquimod: 1-(2-Methylpropyl)-1H-imidazo[4,5-c]quinolin-4-amine) as an active ingredient other than the *Aureobasidium* culture described above.

The following compounds are both known to use TLR7, one of innate immune receptors, as a receptor, and promote inflammatory cytokine via NF-κB (Hiroaki H. et al., Nature Immunology, vol. 3, issue 2, pages 196-200, 2002). On the other hand, the *Aureobasidium* culture according to the present invention activates macrophage phagocytosis by a mechanism different from that of the following compounds and promotes cytokine production in macrophages by a mechanism different from that of the following compounds, as shown in Examples as set forth below. For this reason, when the composition for activating macrophage phagocytosis and/or the composition for promoting cytokine production in macrophages according to the present invention contains the *Aureobasidium* culture and the following compounds, a synergistic effect can be obtained from the macrophage phagocytosis activating action and the cytokine production promoting action.

[Formula 3]

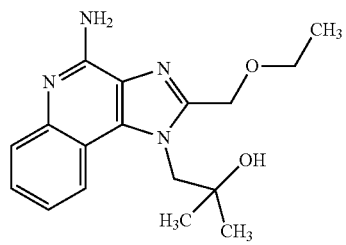

(1)

[Formula 4]

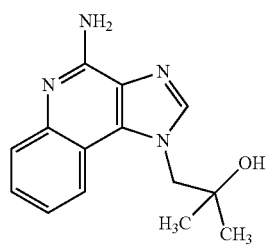

(2)

As the above compound (1) or compound (2), those commercially available can be obtained and used (for example, those manufactured by Wako Pure Chemical Industries, Ltd.). The level to be dosed can be properly determined depending on a difference in purpose of treatment and prevention, level of symptoms, patient age, dosing route, frequency of administration, timing of administration, and the like. The general effective dose level is, for example, when orally taken, it is taken in an amount of about 1 to 5 mg/kg (body weight) per day.

In one embodiment of the composition for activating macrophage phagocytosis of the present invention, the composition is applied to phagocytose cancer cells or cells damaged or killed by an anticancer agent. Specifically, the composition for activating macrophage phagocytosis according to the present invention is administered to a patient during or after anticancer agent treatment. Receptors such as TLR in the innate immune system are thus stimulated, resulting in activation of macrophages. The activated macrophages have a higher expression level of receptors capable of binding to the surface sugar chains or proteins of cancer cells. This can increase its ability to phagocytose cancer cells, and exhibit the effect of decreasing cancer cells.

The cancer cells include cancer cells causing lung cancer, breast cancer, prostate cancer, bladder cancer, ovarian cancer, uterus cancer, colorectal cancer, rectum cancer, colon cancer, small intestine cancer, stomach cancer, esophagus cancer, biliary tract cancer, pancreatic cancer, thyroid cancer, kidney cancer, skin cancer, leukemia, malignant lymphoma, brain tumor, osteosarcoma, head and neck cancer, neuroblastoma, and the like.

Examples of the anticancer agents can include 5-fluorouracil (5-FU), ifosfamide (Ifomide), nimustine hydrochloride (Nidran, cyclophosphamide (Endoxan), dacarbazine (Dacarbazine), melphalan (Alkeran), ranimustine (Cymerin), gemcitabine hydrochloride (Gemzar), enocitabine (Sunrabin), cytarabine ocfosfate (Starasid), cytarabine preparation (Cylocide), tegafur/uracil (UFD), Tegafur/Gimestat/Otastat potassium combined (TS-1), doxifluridine (Furtulon), hydroxycarbamide (Hydrea), methotrexate (Methotrexate), mercaptopurine (Leukerin), idarubicin hydrochloride (Idamycin), epirubicin hydrochloride (Farmorubicin), daunorubicin hydrochloride (Daunomycin), doxorubicin hydrochloride (Adriacin), pirarubicin hydrochloride (Therarubicin), bleomycin hydrochloride (Bleo), peplomycin sulfate (Pepleo), mitoxantrone hydrochloride (Novantron), mitomycin C (Mitomycin S), etoposide (Vepesid, Lastet), irinotecan hydrochloride (Campto), vinorelbine tartrate (Navelbine), docetaxel hydrate (Taxotere), paclitaxel (Taxol), vincristine sulfate (Oncovin), vindesine sulfate (Fildesin), vinblastine sulfate (Exal), oxaliplatin (Elplat), bevacizumab (Avastin) and trastuzumab (Herceptin). Particularly, 5-fluorouracil (5-FU) is preferable.

EXAMPLES

Hereinafter, the present invention will be specifically described with reference to Examples, but these examples are not to be construed as limitations to the scope of the present invention.

Production Example 1

Preparation of *Aureobasidium* Culture Fluid

A culture fluid of *Aureobasidium pullulans* M-1 (FERM BP-08615) was prepared as follows.

A preculture fluid of *Aureobasidium pullulans* M-1 was inoculated in an appropriate amount on a liquid medium (pH 5.3) containing 1% sucrose, 0.1% ascorbic acid, and 0.1% rice bran, and cultured with aeration and stirring at 25° C. for 72 to 96 hours (varies depending on the production batch). After completion of the culture, this culture fluid was sterilized at 121° C. for 15 minutes. The culture fluid obtained after sterilization contained about 1.2% by mass of a solid content, and the content of β-glucan in 100 g of the solid content was 16.7 g. It was contained in an amount of 0.2 g/100 g in terms of the content based on 100 g by mass of the culture fluid itself. The culture fluid was filtered and sterilized with a 0.22-μm filter (Minisart R, Sartorius Biotech, Germany) for use in the following tests.

Test Example 1

Method of Differentiating Human Monocytic Leukemia Cell Line THP-1 into Macrophage-Like Cells In the following Test Examples, the human monocytic leukemia cell line THP-1 or human leukemia T cell line, Jurkat cell line was incubated at 37° C. under 5% $CO_2$ for culture in the RPMI 1640 medium (containing 10% fetal bovine serum (FBS), 75 mg/L kanamycin, and 3.5 μL/L 2-mercaptoethanol).

THP-1 cells (refer to FIG. 1 (A)) were seeded in a 24-well plate (Becton Dickinson Labware, Franklin Lakes, N.J.) at $2\times10^5$ cells/mL per well, and phorbol 12-myristate 13-acetate (PMA) (Wako) was added to each well so as to have a final concentration of 160 nM, and incubated at 37° C. under 5% $CO_2$ for 72 hours, to give macrophage-like cells (refer to FIG. 1 (B)). After incubation, the cells were washed twice with sterilized PBS in order to remove undifferentiated THP-1 cells, and a fresh medium was added thereto, and the mixture was subjected to an experiment.

Test Example 2

Cytotoxicity Test by 5-FU

Figure 2:
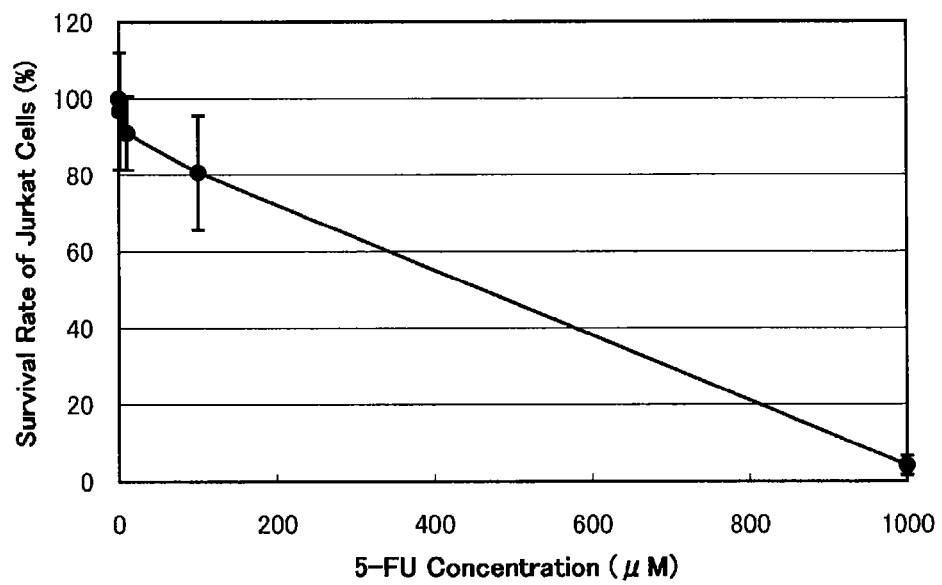
FIG. 2 is a chart showing measurements of cytotoxicity of 5-FU on Jurkat cells.

In order to study the cytotoxicity of 5-FU on Jurkat cells, 5-FU was studied by MTT method. Jurkat cells prepared as $2.0\times10^5$ cells/mL were placed in a 96-well plate (Corning). 5-FU was added thereto so as to have final concentrations of 0, 10, 100, and 1000 μM, and the cells were then exposed thereto in a $CO_2$ incubator at 37° C. for 24 hours. At the time point of the exposure over 23 hours, 10 μL of 3-[4,5-dimethylthiazol-2-yl]-2,5-diphenyltet-razolium bromide (MTT solution) (Wako) was added to each well, and the cells were then exposed thereto at 37° C. for 1 hour. After the exposure, the mixture was centrifuged at 1200 rpm for 5 minutes, the supernatant was discarded, 100 μL per well of DMSO was added, and the mixture was measured for absorbance at 570 nm using a microplate reader. When a tetrazolium salt MTT is taken up by cells, a redox reaction occurs between MTT and NADH to oxidize NADH to $NAD^+$ and reduce MTT to formazan, by the reaction of dehydrogenase present in mitochondria. The formazan is insoluble and precipitates after it is produced. Therefore, DMSO was added to dissolve the formazan precipitate, and the absorbance of the solution was measured at 570 nm. When the cells are alive, formazan is produced, and thus the solution can be measured at 570 nm. As a result, a graph shown in FIG. 2 was obtained, and the $IC_{50}$ was 450 μM.

Test Example 3

Exposure of Phosphatidylserine in Apoptotic Jurkat Cells

Figure 3:
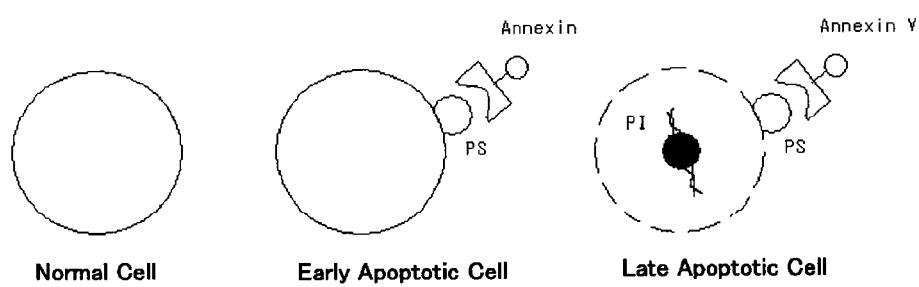
FIG. 3 is a diagram showing a relationship of early apoptotic cells or late apoptotic cells with Annexin V and propidium iodide (PI).
Figure 4:
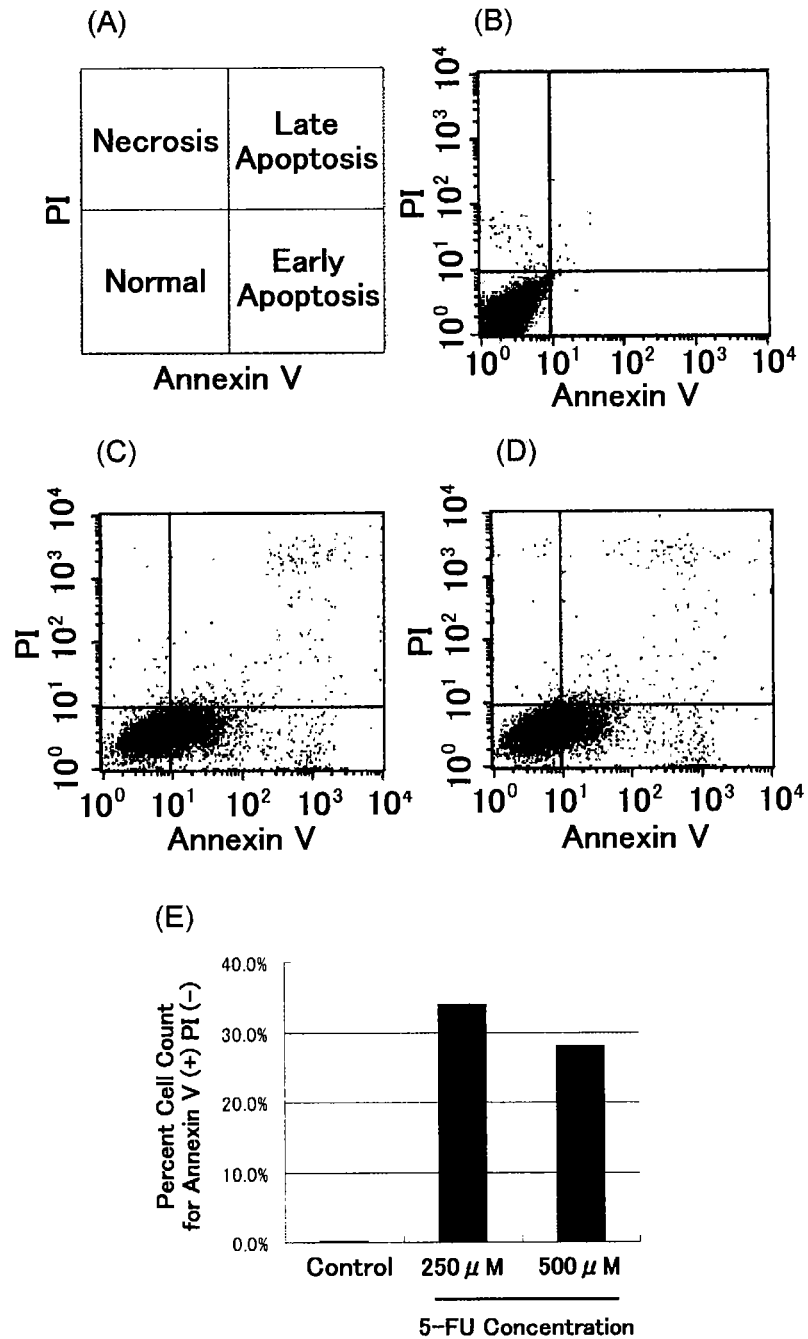
FIG. 4 is charts showing the exposure of phosphatidylserine (PS) in 5-FU attacked Jurkat cells, wherein (A) is an illustration showing how to read the chart, (B) is a chart showing normal Jurkat cells, (C) is a chart showing Jurkat cells which was exposed to 250 μM 5-FU for 24 hours to induce apoptosis, (D) is a chart showing Jurkat cells which was exposed to 500 μM 5-FU for 24 hours to induce apoptosis, and (E) is a chart showing quantitative analysis of Annexin V (+) and propidium iodide (PI) (−) for (A-C) by flow cytometry.

Whether the cytotoxicity of 5-FU on Jurkat cells was caused by apoptosis was studied. In early apoptosis, phosphatidylserine (PS) localized on the inside of cell membrane exposes to the outside. PS is a molecule also relating to the recognition and phagocytosis of apoptotic cells by macrophages. The PS exposure is measured, whereby induction of early apoptosis can be confirmed. In late apoptosis, the cell membrane breaks, and the internal components leak out thereof. Therefore, the cells are combined with propidium iodide (PI) which is a membrane impermeable fluorescent dye, whereby the late apoptotic cells and early apoptotic cells can be clearly separated (refer to FIG. 3). When the cells were exposed to 5-FU at a concentration of 250 μM or 500 μM, it was confirmed that 250 μM 5-FU caused much PS exposure, in other words, induced early apoptosis (refer to FIG. 4).

Test Example 4

Phagocytosis of Macrophage-Like Cells on Jurkat Cells with Early Apoptosis Induced Part 1

The THP-1 cells differentiated into macrophage-like cells were prepared in a 24-well plate by the method of Test Example 1. An *Aureobasidium* culture fluid was added thereto so as to provide a 500-fold dilution, and the mixture was incubated for a total of 7 hours.

Meanwhile, Jurkat cells were exposed for 24 hours to 5-FU at a concentration of 250 μM where early apoptosis was found to be induced in Test Example 2 or 3, and then the Jurkat cells with early apoptosis induced were centrifugally washed twice with PBS. Thereafter, 49.5 μL of PBS was added, 0.5 μL of 0.5 mg/mL 5-(and-6)-carboxytetramethylrhodamine (TAMRA) (Invitrogen) was further added, and the mixture was allowed to react in a dark room for 20 minutes. It is noted that the TAMRA can label Jurkat cells by binding to the cell membrane.

After the reaction, the mixture was centrifugally washed twice with PBS, and 0.5 mL of fresh RPMI 1640 medium was added to make a suspension. 250 μL of the mixture was added to each well in which the above-provided macrophage-like cells exposed to *Aureobasidium* culture fluid for 4 hours had been prepared, and the Jurkat cells with early apoptosis induced were incubated for 3 hours. After the exposure, each well was washed 3 times with sterilized PBS in order to remove Jurkat cells that were not phagocyted. Thereafter, in order to detach adherent macrophage-like cells, 0.5 mL of Trypsin treatment solution (PBS-0.5 mM EDTA+0.05% Trypsin) was added, and the macrophage-like cells were detached using a scraper. In order to stop the action of Trypsin, 0.5 mL of fresh RPMI 1640 medium was added. Thereafter, the mixture was centrifugally washed twice with PBS, and 97 μL of PBS was added to make a suspension, 3 μL of anti-CD 14 antibody-FITC (BD Pharmingen) was added, and the mixture was allowed to react in a dark room for 60 minutes. It is noted that the anti-CD14 antibody-FITC binds to CD14, a membrane protein that expresses on the cell surface of macrophage-like cells, whereby the macrophage-like cells can be specifically labeled.

Figure 5:
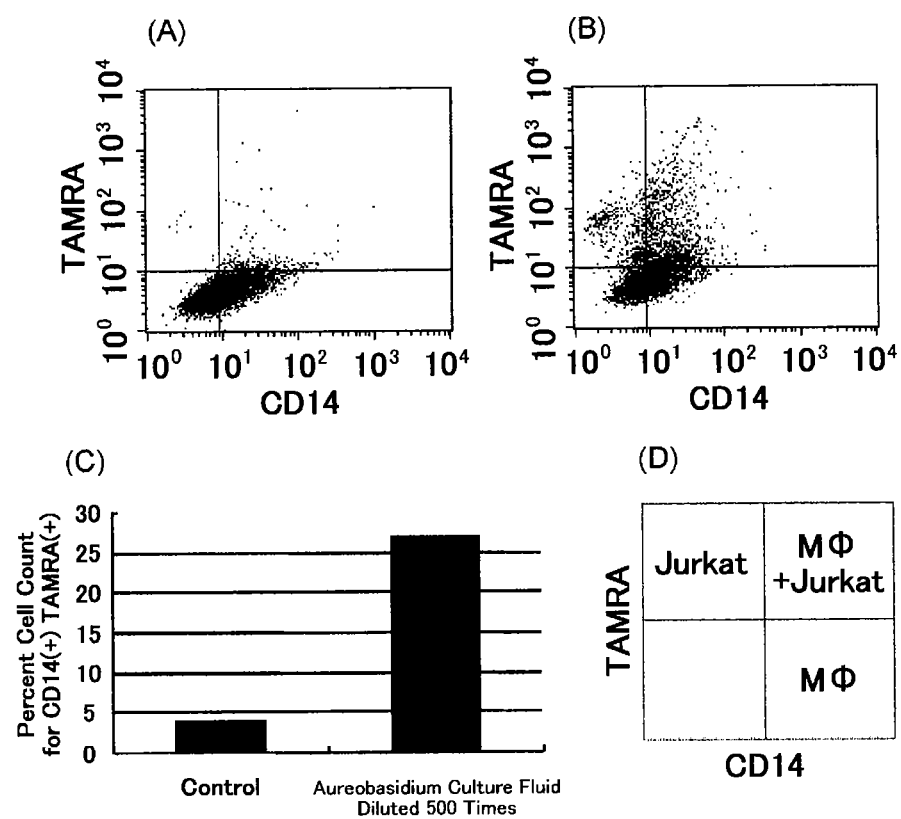
FIG. 5 is charts showing the ability of macrophage-like cells to phagocytose apoptotic Jurkat cells, wherein (A) is a chart showing phagocytosis over a 3-hour period of Jurkat cells where early apoptosis has been induced without anything added, (B) is a chart showing phagocytosis over a 3-hour period of Jurkat cells which have been exposed to a 500-fold dilution of *Aureobasidium* culture fluid for 7 hours to induce early apoptosis, (C) is a chart showing quantitative analysis of double positive regions of CD14 and TAMRA for (A-B) by flow cytometry, and (D) is a chart showing how to read FACS analysis charts.

After the reaction, the mixture was washed twice with PBS. Thereafter, 0.5 mL of PBS was added to make a suspension, and the mixture was analyzed using flow cytometry. Specifically, the macrophage-like cells activated by exposure to a 500-fold dilution of *Aureobasidium* culture fluid for a total of 7 hours were compared with the macrophage-like cells loaded with nothing. As a result, the macrophage-like cells activated by addition of the 500-fold dilution of *Aureobasidium* culture fluid showed about 6-fold phagocytosis as compared to the control. This result indicates that addition of the 500-fold dilution of *Aureobasidium* culture fluid to activate the macrophage-like cells enhanced their ability to phagocytose the Jurkat cells with early apoptosis induced (refer to FIG. 5).

Test Example 5

Ability of Macrophage-Like Cells to Phagocytose Polystyrene Beads

A compound capable of synergistically enhancing the macrophage-activating ability of the *Aureobasidium* culture fluid was explored. Here, the following compound (4-Amino-2-(ethoxymethyl)-a,a-dimethyl-1H-imidazo[4,5-c]quinoline-1-ethanol) (manufactured by Wako Pure Chemical Industries, Ltd.) (hereinafter, referred to as "Compound 1"), an imidazoquinoline derivative that binds to a sugar chain recognition receptor TLR-7 (Toll-like receptor) present in macrophages, was studied.

[Formula 5]

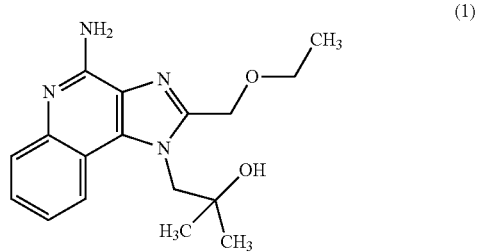

(1)

The THP-1 cells differentiated into macrophage-like cells were prepared in a 24-well plate by the method of Test Example 1. Thereto were each added 500-fold and 1000-fold dilutions as final concentration of an *Aureobasidium* culture fluid, and the mixture was incubated for 4 hours. Also, Compound 1 was prepared with DMSO so as to be 1 mM, and each added to have a final concentration of 1 µM and 10 µM, and the mixture was incubated for 4 hours.

Thereafter, beads with a diameter of 10 µm were added to each well at a final concentration of 2 µL/mL (Trade name "Polybeads dyed violet" manufactured by Polysciences, Inc.), and the mixture was incubated for 3 hours to allow phagocytosis of the beads by the cells. After the incubation, each well was washed 3 times with sterilized PBS in order to remove beads that were not phagocyted. Then, 500 µL of 2.5% p-formaldehyde was added to each well, and the mixture was left at 4° C. for 30 minutes, to fix the cells. The number of beads phagocyted by the macrophage-like cells was measured with a phase contrast microscope. The result was shown by Phagocytic Index (PI: the number of beads phagocyted per 100 cells, phagocyted beads/the number of macrophages).

Figure 6:
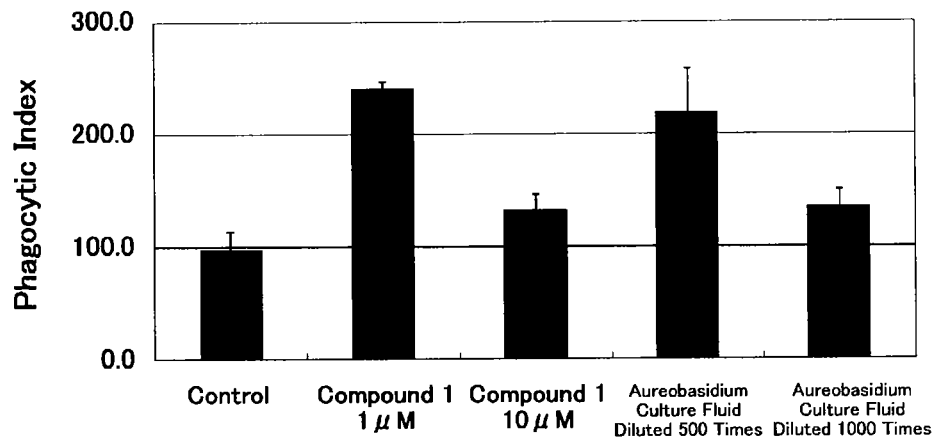
FIG. 6 is a chart showing the ability of macrophage-like cells to phagocytose polystyrene beads.

As shown in FIG. 6, phagocytosis of polystyrene beads was determined for those to which 500-fold and 1000-fold dilutions of *Aureobasidium* culture fluid were added and those to which Compound 1 was added at final concentrations of 1 µM and 10 µM. As a result, in the 500-fold dilution of *Aureobasidium* culture fluid, Phagocytic Index (PI) showed 2.5 times phagocytosis as compared to one with no addition. Also, 1 µM Compound 1 showed phagocytosis similar to the 500-fold dilution of *Aureobasidium* culture fluid. For working concentrations, phagocytosis was higher for the 500-fold dilution in addition of the *Aureobasidium* culture fluid, and it was higher for 1 µM in addition of Compound 1.

Test Example 6

TNF-α Secretion from Macrophage-Like Cells

Since the increase in phagocytosis of macrophage-like cells by the *Aureobasidium* culture fluid or Compound 1 was inferred to be the result of activity induction in the macrophage-like cells, it was attempted to see if it is true. Specifically, regarding TNF-α, a type of cytokines released by activity induction, how much this substance was secreted into a culture fluid of the macrophage-like cells to which the *Aureobasidium* culture fluid, Compound 1, or the *Aureobasidium* culture fluid plus Compound 1 was added was measured by ELISA according to an ordinary method.

Figure 7:
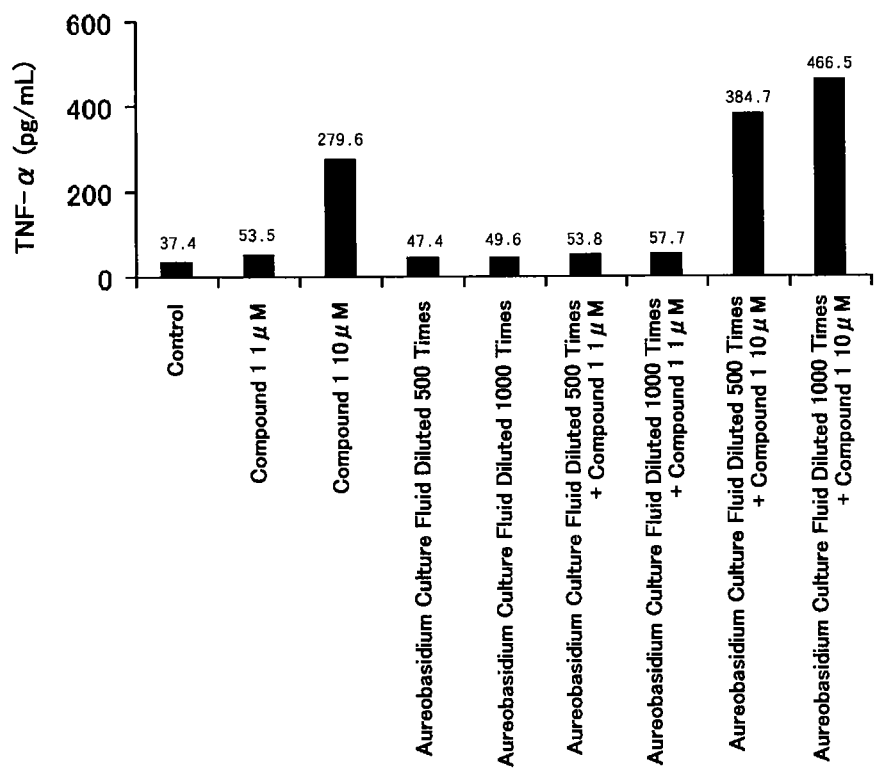
FIG. 7 is a chart showing TNF-α secretion from macrophage-like cells.

As a result, as shown in FIG. 7, it was shown that, when the *Aureobasidium* culture fluid or Compound 1 was each independently added, and when the *Aureobasidium* culture fluid plus Compound 1 was added in combination, TNF-α was secreted in a larger amount, and the macrophage-like cells were activated to a greater extent, as compared to the case of adding nothing. Particularly, it was shown that, when the 500-fold dilution of *Aureobasidium* culture fluid and 10 µM Compound 1 were used in combination, and when the 1000-fold dilution of *Aureobasidium* culture fluid and 10 µM Compound 1 were used in combination, a remarkably large amount of TNF-α was secreted.

Test Example 7

Cytokine Gene Expression in Macrophage-Like Cells

Regarding TNF-α, IL-6, IL-12B, and IL-18, cytokines released when macrophage-like cells underwent activity induction, how much mRNA for these substances expressed in the macrophage-like cells to which the *Aureobasidium* culture fluid, Compound 1, or the *Aureobasidium* culture fluid plus Compound 1 was added was measured by RT-PCR according to an ordinary method.

Specifically, first, the THP-1 cells differentiated into macrophage-like cells by the method of Test Example 1 were washed twice with PBS to remove undifferentiated THP-1 cells, and then divided into 9 groups, group a, group b, group c, group d, group e, group f, group g, group h, and group i. Subsequently, the *Aureobasidium* culture fluid and/or Compound 1 was added to each group so as to have the final concentrations as follows, and the mixture was incubated for 7 hours.

Group a (control): nothing added
Group b: Compound 1 1 µM
Group c: Compound 1 10 µM
Group d: *Aureobasidium* culture fluid diluted 500 times
Group e: *Aureobasidium* culture fluid diluted 1000 times
Group f: *Aureobasidium* culture fluid diluted 500 times+Compound 1 1 µM
Group g: *Aureobasidium* culture fluid diluted 1000 times+Compound 1 1 µM
Group h: *Aureobasidium* culture fluid diluted 500 times+Compound 1 10 µM
Group i: *Aureobasidium* culture fluid diluted 1000 times+Compound 1 10 µM Next, each group was washed with PBS, thereafter, 1 mL of Trizol (Invitrogen) was added to each, and the mixture was well suspended and left at room temperature for 5 minutes. Thereafter, the mixture was transferred to an Eppendorf tube for 1.5 mL, and 200 µL of chloroform (Wako) was added and was vigorously stirred for 20 seconds. After left at room temperature for 2 minutes, the mixture was centrifuged at 12000×g at 4° C. for 10 minutes. After centrifugation, 400 µL of the upper layer was collected and transferred to a new Eppendorf tube for 1.5 mL, and 500 µL of 2-propanol (Wako) was added and stirred, and then left at room temperature for 5 minutes. Thereafter, 200 µl of chloroform was added and was vigorously stirred for 20 seconds. After left at room temperature for 2 minutes, the mixture was centrifuged at 12000×g at 4° C. for 10 minutes. After centrifugation, 400 µL of the upper layer was collected and transferred to a new Eppendorf tube for 1.5 mL, and 500 µL of 2-propanol (Wako) was added and stirred, and then left at room temperature for 5 minutes. Thereafter, the mixture was centrifuged at 12000×g at 4° C. for 10 minutes. After centrifugation, the upper layer was discarded, 75% ethanol was added to the precipitate, and the mixture was centrifuged at 12000×g at 4° C. for 10 minutes. After centrifugation, the upper layer was discarded, and the resultant was suspended in 20 µL of milliQ water, thereby collecting the total mRNA.

Subsequently, using the total mRNA of each group as a template, RT-PCR was performed using TaKaRa RNA PCR Kit (AMV) Ver 3.0 (TaKaRa), to prepare a template cDNA of each sample. The RT-PCR reaction solution composition and RT-PCR reaction conditions are as described below.

RT reaction solution composition: 5 mM $MgCl_2$ 2 µL, RT buffer 1 µL, RNase Free $dH_2O$ 3.75 µL, 1 mM dNTP mixture 1 µL, 1 U/µL RNase inhibitor 0.25 mL, AMV Reverse Transcriptase XL 0.5 µL, oligo dT-Adaptor primer (TaKaRa) 0.5 µL, and the collected total mRNA 1 µL (0.5 µg).

RT reaction conditions: after reaction at 42° C. for 30 minutes, respective reactions at 95° C. for 5 minutes and 5° C. for 5 minutes were performed for 1 cycle using a thermal cycler (Bio Flux).

Subsequently, PCR was performed using the template cDNA of each group as a template, to amplify each cDNA of TNF-α, IL-6, IL-12B, IL-18, and glyceraldehyde-3-phosphate dehydrogenase (GAPDH). Primers, the PCR reaction solution composition, and PCR reaction conditions are as described below.

Primers used for the amplification of cDNA of TNF-α:

```
                                   (SEQ ID NO: 1)
Sense primer;       5'-TCCTTCAGACCCTCAACC-3'

(SEQ ID NO: 2)
1) Antisense primer; 5'-AGGCCCCAGTTTGAATTCTT-3'
```

Primers used for the amplification of cDNA of IL-6:

```
                                   (SEQ ID NO: 3)
Sense primer;     5'-TTTTCTGCCAGTGCCAGTGCCTCTTT-3'

(SEQ ID NO: 4)
Antisense primer; 5'-TACCCCCAGGAGAAGATTCC-3'
```

Primers used for the amplification of cDNA of IL-12B:

```
                                   (SEQ ID NO: 5)
Sense primer;       5'-CATGGGCCTTCATGGTATTT-3'

(SEQ ID NO: 6)
Antisense primer;   5'-TGATGTACTTGCAGCCTTGC-3'
```

Primers used for the amplification of cDNA of IL-18:

```
                                   (SEQ ID NO: 7)
Sense primer;       5'-CAGACCTTCCAGATCGCTTC-3'

(SEQ ID NO: 8)
Antisense primer;   5'-TCGGATTCCAGGTTTTCATC-3'
```

Primers used for the amplification of cDNA of GAPDH:

```
                                   (SEQ ID NO: 9)
Sense primer;       5'-ATCATCAGCAATGCCTCCTG-3'

(SEQ ID NO: 10)
Antisense primer;   5'-CTGCTTCACCACCTTCTTGA-3'
```

PCR reaction solution composition: 5×PCR buffer 10 µL, milliQ 28.75 µL, Ex Taq 0.25 µL, sense primer 0.5 µL, antisense primer 0.5 µL, whole amount of template cDNA of each sample.

PCR reaction conditions: after reaction at 94° C. for 2 minutes, with respective reactions at 94° C. for 30 seconds, 60° C. for 30 seconds, and 72° C. for 1 minute as 1 cycle, 35 cycles were performed.

Thereafter, the amount of PCR reaction product was confirmed by performing agarose gel electrophoresis according to the conventional method, whereby the expression levels of mRNA for TNF-α, IL-6, IL-12B, IL-18, and glyceraldehyde-3-phosphate dehydrogenase (GAPDH) were confirmed.

Figure 8:
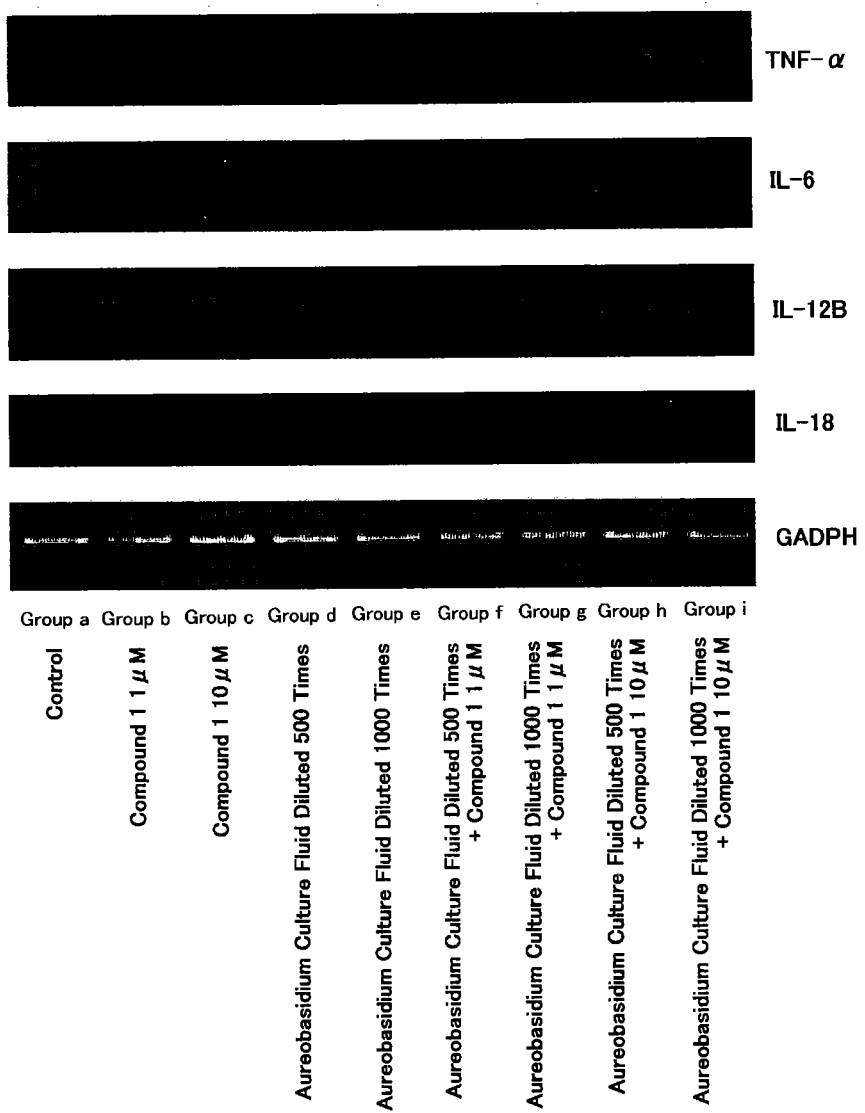
FIG. 8 is a chart showing the results of RT-PCR determination of the expression levels of mRNA for TNF-α, IL-6, IL-12B and IL-18 in macrophage-like cells which have been loaded with *Aureobasidium* culture fluid, Compound 1, or *Aureobasidium* culture fluid plus Compound 1.

As a result, as shown in FIG. 8, it was shown that expression levels of mRNA for TNF-α, IL-12B, and IL-18 in group b, expression levels of mRNA for IL-6, IL-12B, and IL-18 in group c, expression levels of mRNA for IL-12B and IL-18 in group d, and expression levels of mRNA for TNF-α and IL-18 in group e increased as compared to group a (control). It was also shown that expression levels of mRNA for TNF-α, IL-12B, and IL-18 in group f and group g, and expression levels of mRNA for TNF-α, IL-6, IL-12B, and IL-18 in group h and group i increased as compared to group a (control), group b, group c, group d, and group e.

It was shown from these results that the *Aureobasidium* culture fluid and Compound 1 both promoted the production of cytokines in macrophage-like cells. In addition, it was shown that when the *Aureobasidium* culture fluid and Compound 1 were used in combination, the production of more kinds of cytokines was promoted, and the production amount of cytokines increased more, as compared to the case where the *Aureobasidium* culture fluid or Compound 1 was independently used. In other words, it was shown that the *Aureobasidium* culture fluid and Compound 1 had each a different mechanism for promoting cytokine production, and use of them in combination could create a synergistic effect.

Test Example 8

Phagocytosis of Macrophage-Like Cells on Jurkat Cells with Early Apoptosis Induced Part 2

The THP-1 cells differentiated into macrophage-like cells were prepared in a 24-well plate by the method of Test Example 1. Thereto were each added the *Aureobasidium* culture fluid to provide a 1000-fold dilution, Compound 1 to provide a 1-W solution, and the *Aureobasidium* culture fluid to provide a 1000-fold dilution plus Compound 1 to provide a 1-W solution, and the mixtures were incubated for 4 hours.

Meanwhile, 5-FU was caused to act on Jurkat cells for 24 hours at a concentration of 250 µM where early apoptosis was shown by Test Example 2 or 3 to be induced, and the Jurkat cells with early apoptosis induced were centrifugally washed twice with PBS. Thereafter, 49.5 µL of PBS was added, 0.5 µL of 0.5 mg/mL 5-(and-6)-carboxytetramethylrhodamine (TAMRA) (Invitrogen) was further added, and the mixture was reacted in a dark room for 20 minutes. It is noted that the TAMRA can label Jurkat cells by binding to the cell membrane.

After reaction, the mixture was centrifugally washed twice with PBS, and 0.5 mL of fresh RPMI 1640 medium was added to make a suspension. 250 µL of the mixture was added to each well in which the above-provided macrophage-like cells exposed to *Aureobasidium* culture fluid for 4 hours had been prepared, and the Jurkat cells with early apoptosis induced were incubated for 3 hours. After the exposure, each well was washed 3 times with sterilized PBS in order to remove Jurkat cells that were not phagocyted. Thereafter, in order to detach adherent macrophage-like cells, 0.5 mL of Trypsin treatment solution (PBS-0.5 mM EDTA+0.05% Trypsin) was added, and the macrophage-like cells were detached using a scraper. In order to stop the action of Trypsin, 0.5 mL of fresh RPMI 1640 medium was added. Thereafter, the mixture was centrifugally washed twice with PBS, and 97 μL of PBS was added to make a suspension, 3 μL of anti-CD14 antibody-FITC (BD Pharming) was added, and the mixture was allowed to react in a dark room for 60 minutes. It is noted that the anti-CD14 antibody-FITC binds to CD14, a membrane protein that expresses on the cell surface of macrophage-like cells, whereby the macrophage-like cells can be specifically labeled.

Figure 9:
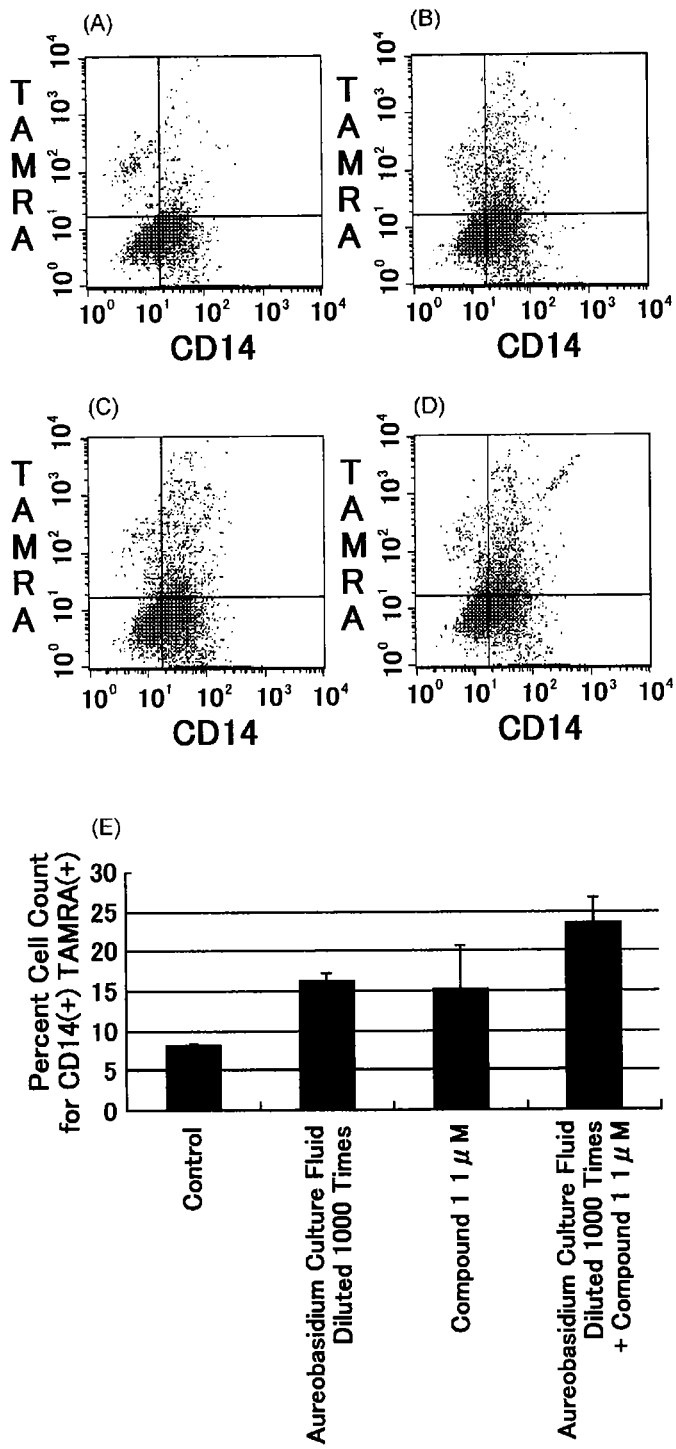
FIG. 9 is charts showing the ability of macrophage-like cells to phagocytose apoptotic Jurkat cells, wherein (A) is a chart showing phagocytosis by macrophages of Jurkat cells over a 3-hour period where early apoptosis has been induced, the macrophages having not been loaded with anything, (B) is a chart showing phagocytosis by macrophages of Jurkat cells over a 3-hour period where early apoptosis has been induced, the macrophages having been exposed to a 1000-fold dilution of *Aureobasidium* culture fluid for a total of 7 hours, (C) is a chart showing phagocytosis by macrophages of Jurkat cells over a 3-hour period where early apoptosis has been induced, the macrophages having been exposed to 1 μM Compound 1 for a total of 7 hours, (D) is a chart showing phagocytosis by macrophages of Jurkat cells over a 3-hour period where early apoptosis has been induced, the macrophages having been exposed to a 1000-fold dilution of *Aureobasidium* culture fluid plus 1 μM Compound 1 for a total of 7 hours, and (E) is a chart showing quantification for A-D.

After the reaction, the mixture was washed twice with PBS. Thereafter, 0.5 mL of PBS was added to make a suspension, and the mixture was analyzed using flow cytometry. As a result, the macrophage-like cells loaded with the 1000-fold dilution of *Aureobasidium* culture fluid plus 1 μM Compound 1 showed a higher phagocytosis than the macrophage-like cells loaded only with the *Aureobasidium* culture fluid or the macrophage-like cells loaded only with Compound 1 (refer to FIG. 9). In other words, it was indicated that, since the *Aureobasidium* culture fluid and Compound 1 had different mechanisms for activation of macrophage phagocytosis, use of them in combination could create a synergistic effect in the action of macrophage phagocytosis activation.

The invention claimed is:

1. A method for activating macrophage phagocytosis by macrophages or macrophage-like cells or promoting cytokine production in macrophages or macrophage-like cells, comprising:

(a) obtaining a culture by culturing a microorganism belonging to *Aureobasidium* sp.; and (b) administering to the macrophages or macrophage-like cells a composition comprising said culture and compound (1)

[Formula 1]

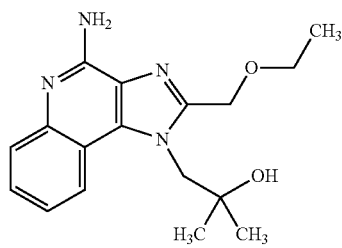

(1)

wherein the microorganism belonging to *Aureobasidium* sp. is *Aureobasidium pullulans* M-1 (FERM BP-08615), wherein the composition comprises Compound 1 at 10 μM, wherein the composition is in an amount effective for activating macrophage phagocytosis synergistically by the macrophages or macrophage-like cells or promoting cytokine production synergistically in macrophages or macrophage-like cells.

* * * * *